US00PP18003P2

(12) United States Plant Patent
Lintott

(10) Patent No.: US PP18,003 P2
(45) Date of Patent: Sep. 11, 2007

(54) *CHRYSANTHEMUM* PLANT NAMED 'APENNINE'

(50) Latin Name: *Chrysanthemum morifolium*
Varietal Denomination: Apennine

(75) Inventor: Keith G. Lintott, Bognor Regis (GB)

(73) Assignee: Cleangro Ltd., Chichester, West Sussex (GB)

( * ) Notice: Subject to any disclaimer, the term of this patent is extended or adjusted under 35 U.S.C. 154(b) by 0 days.

(21) Appl. No.: 11/396,882

(22) Filed: Apr. 3, 2006

Related U.S. Application Data

(60) Provisional application No. 60/669,804, filed on Apr. 7, 2005.

(51) Int. Cl.
*A01H 5/00* (2006.01)

(52) U.S. Cl. ..... Plt./294

(58) Field of Classification Search ..... Plt./294
See application file for complete search history.

(56) References Cited

U.S. PATENT DOCUMENTS

PP8,935 P 10/1994 Vandenburg ..... Plt./74.1

PP15,349 P2 11/2004 Kester ..... Plt./297

OTHER PUBLICATIONS

2004 Cleangro Brochure listing the *Chrysanthemum* variety 'Effect'. See photograph at p. 2. Brochure was published Sep. 1, 2003.

2005 Cleangro Brochure listing the *Chrysanthemum* variety 'Effect'. See, e.g., photographs at pp. 1 and 4. Brochure was published Sep. 1, 2004.

2004 Ficor Catalogue listing the *Chrysanthemum* variety 'Effect'. See, e.g., photographs on inside of front cover, and listings at pp. 2 and 11. Catalogue was published Oct. 1, 2003.

2005 Ficor Catalogue listing the *Chrysanthemum* variety 'Effect' at pp. 5 and 11 and the variety 'Le Mans' at pp. 5 and 14. Catalogue was published Jan. 25, 2005.

1998 Ficor Catalogue listing a new *Chrysanthemum* variety 'Le Mans' at pp. 4 and 9. Catalogue was published Oct. 30, 1997.

2003 GroLink *Chrysanthemums* Pot Mum Catalog listing a *Chrysanthemum* variety 'Le Mans'. See, e.g., photograph at p. 9 and listings at pp. 22 and 24.

*Primary Examiner*—Kent L. Bell
*Assistant Examiner*—Annette H Para
(74) *Attorney, Agent, or Firm*—Winston & Strawn, LLP

(57) ABSTRACT

A new variety of *Chrysanthemum* plant named 'Apennine', having a flat capitulum, medium vigor and upright growth habit and medium white-green anemone type flowers.

1 Drawing Sheet

Latin name of the genus and species: Botanical classification: *Chrysanthemum morifolium.*

Variety denomination: The new *Chrysanthemum* variety denomination is 'Apennine'.

BACKGROUND OF THE INVENTION

The present invention comprises a new and distinct cultivar of *Chrysanthemum* botanically known as *Chrysanthemum morifolium,* and referred to by the cultivar name 'Apennine'.

'Apennine', identified as 14672-0 originated from a cross made in a controlled breeding program in Chichester, West Sussex, United Kingdom.

The female parent of the new variety is identified as 12748-0 is an undistributed, unpatented seedling and the male parent is the unpatented variety known as 'Le Mans.' The new variety 'Apennine' has been asexually reproduced by vegetative cuttings, in Chichester, West Sussex, United Kingdom and the distinguishing characteristics are retained through successive generations of asexual reproduction.

BRIEF SUMMARY OF THE INVENTION

'Apennine' is a cut type of *Chrysanthemum* plant variety having a flat capitulum form and white petal-green cushion anemone type flowers.

Comparison with Female Parent

Plants of the new *Chrysanthemum* variety 'Apennine' are similar to the female parent 12748-0 in plant habit and growth rate. However, in side-by-side comparisons in Chichester, West Sussex, United Kingdom, under commercial practice, plants of the new *Chrysanthemum* variety 'Apennine' differed from plants of the female parent 12748-0 in the following characteristics:

1. The new variety 'Apennine' produces white-green anemone type flowers whereas the female parent 12748-0 produces light pink, pink anemone type flowers.
2. Plants of the new variety 'Apennine' have larger and shorter inflorescence than plants of the female parent 12748-0.
3. Plants of the new variety 'Apennine' have smaller green foliage than plants of the female parent 12748-0.

Comparison with Male Parent

Plants of the new *Chrysanthemum* variety 'Apennine' are similar to the male parent 'Le Mans' in plant habit and growth rate. However, in side-by-side comparisons in Chichester, West Sussex, United Kingdom, under commercial practice, plants of the new *Chrysanthemum* variety 'Apennine' differed from plants of the male parent 'Le Mans' in the following characteristics:

1. The new variety 'Apennine' produces white-green anemone type flowers whereas the male parent 'Le Mans' produces pink-white anemone type flowers.
2. Plants of the new variety 'Apennine' have larger and taller inflorescence than plants of the male parent 'Le Mans'.
3. Plants of the new variety 'Apennine' have a 52 Short Day response whereas plants of the variety 'Le Mans' have a 48 day response.

Comparison with the *Chrysanthemum* variety 'Effect'

Plants of the new *Chrysanthemum* variety 'Apennine' are dissimilar to plants of the unpatented variety 'Effect' in plant habit and growth rate. In side-by-side comparisons in Chichester, West Sussex, United Kingdom, under commercial practice, plants of the new *Chrysanthemum* variety 'Apennine' differed from plants of 'Effect' in the following characteristics:

1. The new variety 'Apennine' produces medium sized white-green anemone type flowers whereas 'Effect' produces large sized white-green anemone type flowers.
2. Plants of the new variety 'Apennine' have smaller and shorter inflorescence than plants of 'Effect'.
3. Plants of the new variety 'Apennine' have lighter and smaller foliage than plants of 'Effect'.
4. The new variety 'Apennine' has a 52 Short Day response whereas plants of the variety 'Effect' have a 56 Short Day response.

BRIEF DESCRIPTION OF ILLUSTRATIONS

Typical specimens of the plant and flowers for the new *Chrysanthemum* variety 'Apennine' are shown in the accompanying scanned image printed from a photograph. The colors shown are as true as possible within the usual limits of this kind of illustration.

FIG. 1 is a side perspective view of a typical flowering stem of the new variety grown as a cut flower. The plant shown in the illustration is 52 days from the onset of Short Days.

DETAILED BOTANICAL DESCRIPTION

The following description of the new *Chrysanthemum* variety 'Apennine' is of plants grown in the soil in a greenhouse in Chichester, West Sussex, United Kingdom, in the month of February. The cultivar has not been observed under all possible environmental conditions. The phenotype may vary significantly with variations in the environment such as temperature, length of day and light intensity, without any variance in genotype. The commercial classification of the new variety is a cut flower *Chrysanthemum.*

Plants of the new variety have been grown successfully under temperature conditions averaging about 18° C. at night and about 18° C. to 24° C. during the day under light conditions of about 5,000 to 6,000 foot candles. The plants respond well to the use of growth retardant, such as one B9 treatment at about two grams/liter. To produce a commercial product, the plants should not be pinched or the center bud removed. It has been observed that the shelf life of the new variety is about 18 days with a response time of about 7½ weeks. The new variety is suitable for growth in a temperature range of 18° C. to 24° C.

The new variety may be produced as a spray. The following description is with respect to a plant produced as spray *Chrysanthemum.* In the description of this new *Chrysanthemum* variety, color values have been taken from The Royal Horticultural Society Colour Chart (R.H.S.C.C.).

Plant

Plant type: Anemone flower type of cut *Chrysanthemum.*
Habit: Upright.
Height (cm): 80–100.
Width (cm): 25–35.
Stem:
- *Length* (*cm*).—75–95.
- *Diameter* (*cm*).—0.6–0.8.
- *Texture.*—Smooth, slightly pubescent.
- *Color.*—Near 139C.

Branching characteristics:
Lateral branches:
- *Length* (*cm*).—6–11.
- *Diameter* (*cm*).—0.2–0.25.
- *Texture.*—Smooth, slightly pubescent.

Number of breaks from pinch: Not pinched.
Response time: 52 days.
Vigor: Medium.
Shelf life: 18 days.
Life of blooms: 18 days.
Disease (susceptibility/resistance observed): None observed to date.
Pest (susceptibility/resistance observed): None observed to date.
Drought and temperature (susceptibility/resistance observed): None observed to date.
Growth retardant type and treatment: 1 application of 2 gm/liter B9 @ 21 days after sticking unrooted cuttings.
The plants were grown for 2 weeks in Long Day conditions (20 hours of light) and then transferred to Short Day conditions (13 hours of dark).
Propagation:
- *Type.*—Vegetative propagation via stem cuttings.
- *Time to rooting.*—12 days with soil temperatures of 22° C.
- *Rooting habit.*—After 7 Long Days, the first roots emerge and form root primordia. In 12 Long Days, a complete root system is developed.

Foliage

Number of leaves per lateral branch: 28–35.
Compound or single: Single.
Arrangement of leaves: Alternate.
- *Shape of leaf.*—Typically 5 lobed.
- *Size of leaf.*—Width (cm) 4–7. Length (cm): 9–11.
- *Leaf apex.*—Mucronate.
- *Base.*—Asymmetric.
- *Attachment.*—Petioled.
- *Aspect.*—Slightly undulating.
- *Margin.*—Palmately lobed.
- *Surface characteristics.*—Top: Slightly pubescent. Bottom: Veined, slightly pubescent.

Petiole:
- *Color.*—Near 137D.
- *Length* (*cm*).—2–3.
- *Diameter* (*cm*).—0.3–0.4.
- *Surface.*—Smooth, slightly pubescent.

Venation: Net, prominent lateral and mid-veins at underside.
*Color.*—Upper side: near 139D. Under side: near 139D.
Color:
*Mature leaf, upper side.*—Near 137A; under side: near 137C.
*Young leaf, upper side.*—Near 137D; under side: near 137D.

Flower

Flower appearance: Matte.
Flower type: Anemone.
Flower form: Slightly cupped.
Flower shape: Round.
Flowering habit: Cylindrical.
Number of blossoms per branch: 7–11.
Typical and observed flowering season: Year Round.
Inflorescence form: Corymbiform.
*Depth of fully expanded blossoms* (*cm*).—1.5–2.0.
*Diameter of fully expanded blossoms* (*cm*).—5.5–7.0.
*Anemone center diameter* (*cm*).—2.5–3.0.
Phyllaries:
*Number.*—28–32.
*Color.*—Near 137A.
*Length* (*cm*).—0.5–0.8.
*Width* (*cm*).—0.1–0.3.
*Texture/Appearance.*—Dull, slightly pubescent.
Pedicel:
*Length* (*cm*).—5.5–11.
*Diameter* (*cm*).—0.2–0.3.
*Angle from stem* (*degrees*).—20–25.
*Color.*—Near 137C.
*Surface.*—Smooth, slightly pubescent.
*Habit.*—Slightly curving.
*Strength.*—Strong.
Ray florets:
*Form/shape.*—Straight.
*Texture/appearance.*—Dull, slightly ridged.
*Number per flower.*—22–25.
*Length* (*cm*).—2.5–3.0. Width (cm): 0.5–0.7.
*Apex.*—Round.
*Base.*—Tubular.
*Margin.*—Entire.

Disc florets:
*Form/shape.*—Tubular, dentate ends.
*Texture/appearance.*—Dull, smooth.
*Number per flower.*—120–130.
*Length* (*cm*).—1–1.7; Width (cm): 0.1–0.2.
*Diameter of disc* (*cm*).—0.5–0.6.
Fragrance: None.
Flower bud (at onset of color):
*Length* (*cm*).—1.
*Diameter* (*cm*).—1.
*Form/shape.*—Globular.
General flower color:
*1. Ray florets, upper side.*—Immature: near 155B. Mature: near 155B. Older/Fading: near 155B.
*2. Ray florets, under side.*—Immature: near 155B. Mature: near 155B. Older/Fading: near 155B.
*3. Disc florets.*—Immature: tube near 150D,tip near 140B. Mature: tube near 150D, tip near 140B. Older/Fading: tube near 150D,tip near 140B.
*6. Bud.*—Near 137A.
Flower progression with age: No fading with age.

Reproductive Organs

Gynoecium present on Ray and Disc florets.
Ray florets per individual flower: Pistillate.
*Pistil number.*—22–25 observed.
*Stigma color.*—Near 151B.
*Stigma shape.*—Forked.
*Style color.*—Near 151B.
*Style length* (*cm*).—0.2–0.4.
Disc florets per individual flower: Pistillate.
*Pistil number.*—120–130 observed.
*Stigma color.*—Near 151B.
*Stigma shape.*—Forked.
*Style color.*—Near 151B.
*Style length* (*cm*).—0.2–0.3.
Androecium: Not observed.
Fruit and seeds: None observed.

What is claimed is:

1. A new and distinct variety of *Chrysanthemum* plant, substantially as described and illustrated herein.

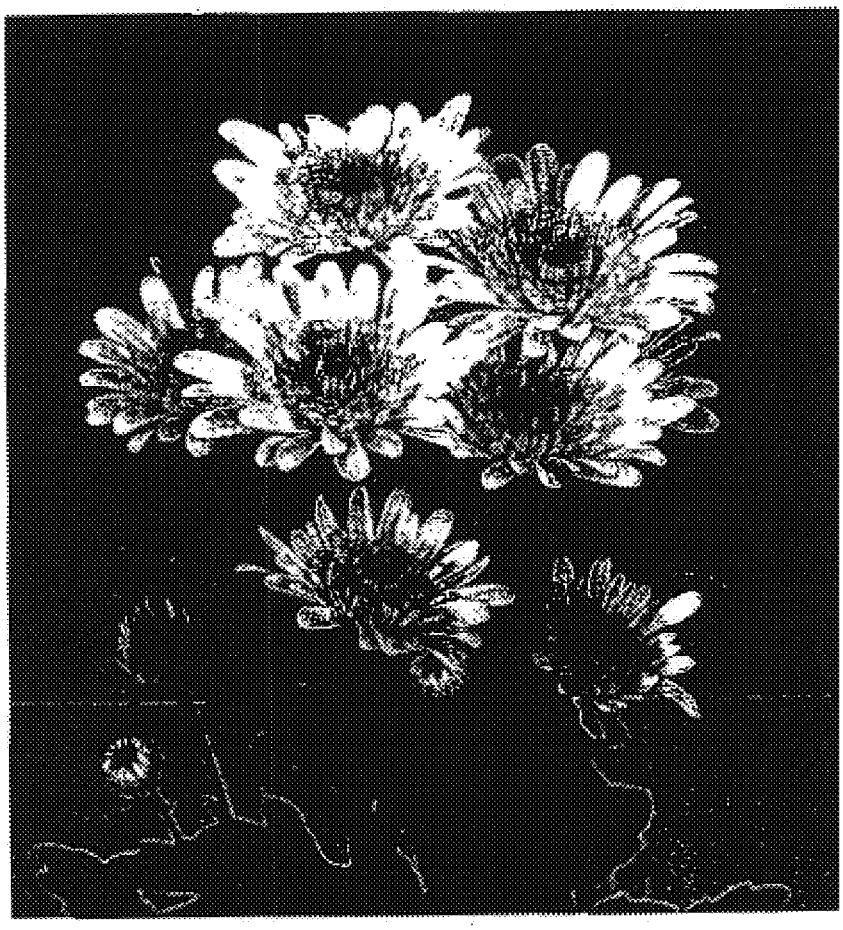

* * * * *